Figure 11:
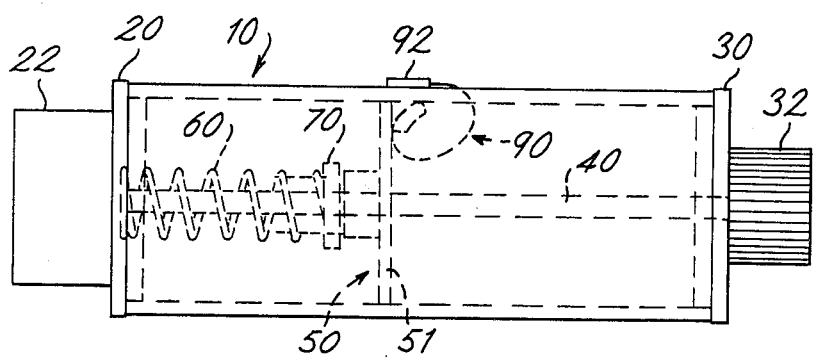

United States Patent [19]

Wright

[11] 3,958,565
[45] May 25, 1976

[54] VENTILATORY CAPACITY MEASURING INSTRUMENT

[75] Inventor: Basil Martin Wright, Rickmansworth, England

[73] Assignee: National Research Development Corporation, London, England

[22] Filed: July 12, 1974

[21] Appl. No.: 488,243

[30] Foreign Application Priority Data
July 17, 1973 United Kingdom............... 33934/73

[52] U.S. Cl................................. 128/2.08; 73/239; 272/99
[51] Int. Cl.²......................................... A61B 5/08
[58] Field of Search........................ 128/2.08, 2 C; 252/57 F; 73/419, 239

[56] References Cited
UNITED STATES PATENTS

| | | | |
|---|---|---|---|
| 471,389 | 3/1892 | Lacey | 128/2.08 |
| 1,541,750 | 6/1925 | Park | 73/419 |
| 3,298,362 | 1/1967 | Lippett, Jr. et al. | 128/2.08 |
| 3,635,214 | 1/1972 | Rand | 128/2.08 |
| 3,720,202 | 3/1973 | Cleary | 128/2.08 |
| 3,826,247 | 7/1974 | Ruskin et al. | 128/2.08 |
| 3,862,628 | 1/1975 | Williams | 128/2.08 |

FOREIGN PATENTS OR APPLICATIONS

| | | | |
|---|---|---|---|
| 1,160,669 | 8/1969 | United Kingdom | 128/2.08 |
| 267,933 | 6/1927 | United Kingdom | 272/57 F |

*Primary Examiner*—Robert W. Michell
*Assistant Examiner*—Lee S. Cohen
*Attorney, Agent, or Firm*—Cushman, Darby & Cushman

[57] ABSTRACT

A human ventilatory capacity measurement instrument, of the kind which measures the peak flow rate of a single forced expiration, comprises a hollow cylindrical body housing a coaxial rod on which is carried a piston spring-biased in one longitudinal sense. The body is longitudinally slotted and has an indicator engaged in the slot for movement therealong by the piston when blown against its spring bias, but the indicator is returned to its starting position in the slot by independent movement. A scale is provided alongside the slot to give a measure of peak flow rate by the final rest position of the indicator when pushed by the piston.

3 Claims, 16 Drawing Figures

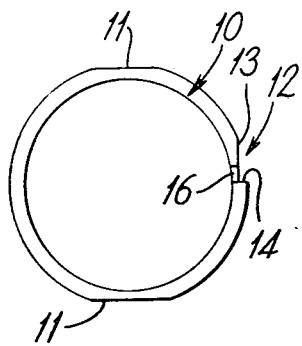
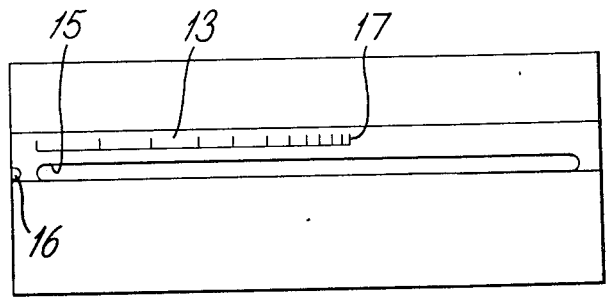
Fig. 1a        Fig. 1b
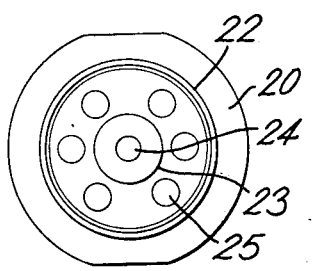 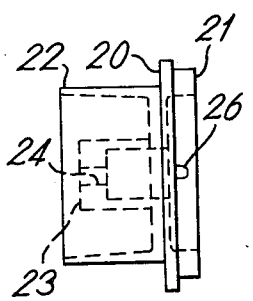 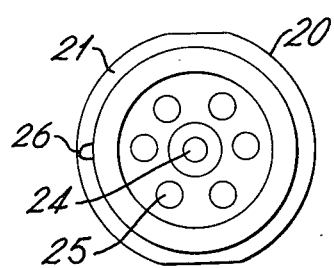
Fig. 2a        Fig. 2b        Fig. 2c
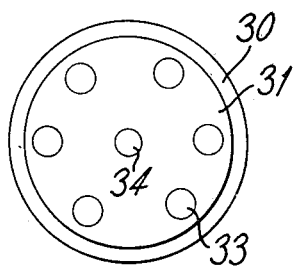 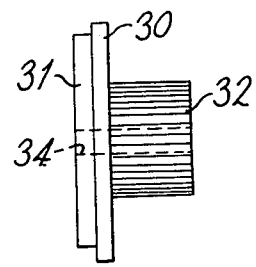 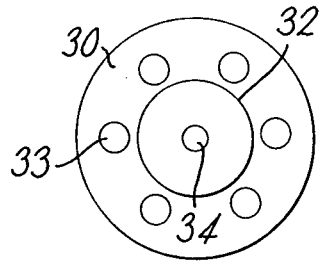
Fig. 3a        Fig. 3b        Fig. 3c

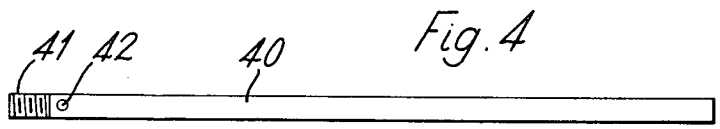
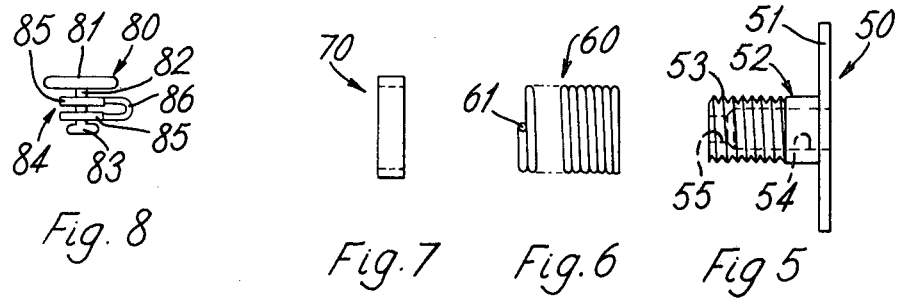
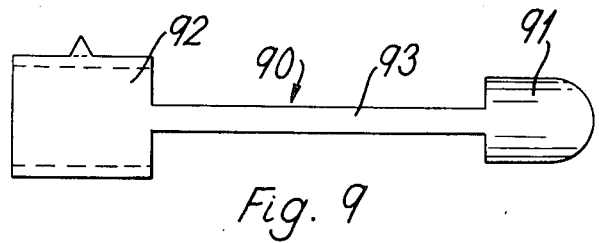
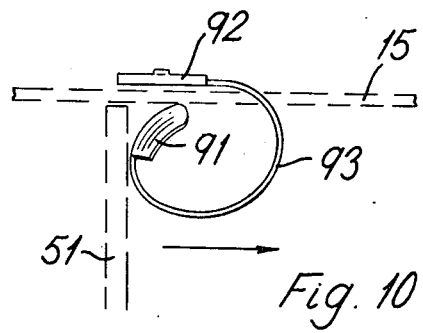

VENTILATORY CAPACITY MEASURING INSTRUMENT

This invention concerns human ventilatory capacity measurement instruments and more particularly such instruments of the kind which measure the maximum or peak flow rate of a single forced expiration.

According to the present invention an instrument of the kind in question comprises: a hollow cylindrical body; a rod mounted substantially coaxially within said body; a piston slidably mounted on said rod; spring means connected between said piston and said body, in the annular space between said body and rod, to apply a progressively increasing bias against movement of said piston from one end to the other end of said body; a slot formed in and extending along said cylinder; an indicator member mounted in said slot for movement therealong towards said body other end by engagement with said piston, but separate movement towards said body one end; and a scale on said body alongside said slot.

In use of the proposed device a forced expiration is applied to the body one end to impel the piston against the spring bias. As the piston is impelled it moves the indicator along the slot and also exposes more of the slot to vent the expired air from the cylinder in progressively increasing manner. Thus, the piston travels to the point at which the venting of the body balances the expired air input and then subsequently returns under spring action while the indicator member remains to mark the point of maximum travel relative to the scale.

For a fuller understanding of the invention one embodiment thereof will now be described with reference to the accompanying drawings, in which:

FIGS. 1a and 1b respectively illustrate the body of the embodiment in end and side elevations;

FIGS. 2a, 2b and 2c respectively illustrate an end member for the body in one end, side, and opposite end elevations;

FIGS. 3a, 3b and 3c similarly illustrate another end member for the body;

FIGS. 4 to 8 respectively illustrate the rod, piston, spring, a spring connecting member, and the indicator member of the embodiment;

FIGS. 9 and 10 illustrate an alternative indicator member, and FIG. 11 is a side view illustrating the assembled device of the present invention.

Referring to the drawings, the body of FIG. 1 comprises a right circular, hollow, cylindrical body 10 having two diametrally-opposed flats 11 formed axially along its outer surface. The body outer surface is also formed with an axially-directed groove 12 therein, the groove having a flat base 13 and a shoulder 14 along only one side thereof, and being located approximately centrally between the two flats 11 in the circumferential direction around the body. Lastly, the body is formed with an axially-directed slot 15 extending between points adjacent the ends of the groove 12, a notch 16 in one end of the groove 12, and a scale 17 located on the groove base 13 alongside the slot 15.

The first end member, illustrated by FIG. 2, comprises a circular disc 20 with flats corresponding to those of the body, and having shorter and longer hollow circular cylindrical bosses 21 and 22 extending coaxially from respectively opposite sides thereof. The diameter of the disc 20 is equal to the external diameter of the body, and the external diameter of the shorter boss 21 is equal to the internal diameter of the body. The longer boss 22 is hollowed in convergently tapered form towards the disc 20, and is formed with a plug 23 extending coaxially partway therealong from the disc. The plug 23 is hollowed to communicate, through the disc 20, with the hollow of the shorter boss 21, part of the former hollowing consisting of a tapped coaxial bore 24 in the end wall of the plug remote from the disc 20. The disc 20 and the adjoining end wall of the longer boss 22 bordering the annular gap between the radially outer wall and plug of the latter is formed with six axially-directed apertures 25 therethrough, these apertures being uniformly spaced in a circumferential sense around the end member. Lastly, a key member 26 is formed on the outer surface of the shorter boss 21 to extend radially outwardly along the adjoining face of the disc 20, this key member being complementary with the notch 16 of the body 10.

The second end member, illustrated by FIG. 3, also comprises a circular disc 30 having opposed shorter and longer circular cylindrical bosses 31 and 32 extending coaxially from respectively opposite sides thereof. The external diameters of the disc 30 and shorter boss 31 respectively equal the external and internal diameters of the body 10, and the longer boss 32 is of smaller diameter than the shorter boss 31. The disc 30 and shorter boss 31 are formed with a plurality of axially-directed bores 33 therethrough, in a uniform annular array extending circumferentially therearound at locations radially beyond the longer boss 32, and the disc and both bosses are coaxially bored at 34 to a diameter slightly less than that of bore 24 in the first end member. Lastly, the longer boss is externally knurled to facilitate manual gripping thereof.

The rod of FIG. 4 is of circular cylindrical form denoted at 40 having equal diameter with the bore 24 of the first end member, and is threaded over a short length 41 at one end thereof in corresponding manner with such bore. The rod is also formed with a diametral bore 42 adjacent said length 41.

The piston of FIG. 5 is denoted at 50 in the form of a circular disc 51 having a boss 52 extending coaxially from one side thereof. The boss 52 is of reduced external diameter over an end portion 53 thereof remote from the disc, which portion is threaded. Also, the disc 51 and boss 52 are coaxially bored at 54, an end portion 55 of this bore remote from the disc 51 being of a reduced diameter equal to that of the rod 40.

The spring of FIG. 6 is a tension spring 60 of helical form having one end portion 61 which terminates diametrally.

The spring connecting member of FIG. 7 is a sleeve 70.

The indicator member of FIG. 8 comprises a stud 80 having an end plate 81 serving as a pointer, a stem 82 projecting perpendicularly from the plate and an enlarged end portion 83 for the stem. The stud is also associated with a spring 84 in the form of two washers 85 integrally connected by a strip 86 therebetween, the washers snapping over the stem end portion 83 with the strip 86 bent to spring the washers into mutually separated positions on the stem.

Assembly of the embodiment of FIGS. 1 to 8 comprises pressfitting of the non-threaded end of the rod in the second end member bore 34 with the rod extending from the boss 31. The open circular end of the spring 60 is screwed on to the threaded portion 53 of the piston 50 and the sleeve is located over the end of the spring engaged around the piston portion 53 to assist in securing the spring. The piston and spring assembly is then slid on the rod 40, piston disc 51 first, and the diametral end 61 of the spring 60 engaged in the rod bore 42. Then the boss 21 of the first end member is engaged in the notched end of the body 10 with the key member 26 received in the relevant notch 16, and the second end member is engaged in the other end of the body to allow threaded engagement of the rod portion 41 in the tapped bore of such member. Before this last engagement the indicator member stud 80 is passed through the body slot 15 with the plate 81 outermost, and the associated spring 84 snapped on the stud from within the body to spring load the stud on the cylinder.

In use of the assembled instrument a disposable mouthpiece (not shown), of the kind employed with existing peak ventilatory flow measuring instruments, is engaged in the tapered hollow of the first end member boss 22, the indicator member is set to zero on the scale 17 by abutting the same against the piston, and the patient effects a forced expiration into the mouthpiece. As discussed generally hereinbefore, the expired air passes into the body through the first end member apertures 25 to impel the piston along its rod against the bias of the spring 60 until the increasing venting effect of the slot 15 balances the air input. On termination of the expiration, the piston returns under spring action but leaves the indicator member stud positioned to mark the peak air flow relative to the scale.

The structure of the invention as exemplified by this embodiment is advantageous in its compactness, and simplicity and economy of manufacture compared with existing instruments. The compactness stems from the generally cylindrical nature of the instrument which is easily gripped and applied to the mouth, and from the fact that all moving parts are confined within the bounds of the cylindrical shape. As to simplicity and economy of manufacture: it will be seen that all parts with the exception of the helical spring 60 can be made by moulding from plastics material with the requirements for machining and like operations being reduced to a minimum.

In addition, it is to be noted that the relevant embodiment can be readily disassembled for cleaning.

Also, it is preferred that the slot be of uniform width and that the spring be of substantially constant rate, so that, in the result, the piston movement has a curvilinear relationship with expiration flow rate. Accordingly, the scale is of corresponding curvilinear form and it is possible to accommodate a range of flow rates which take account of child and adult use of a single instrument. This has been confirmed during development of the invention with an instrument of the form just described having overall dimensions of about 140mm length and 45mm diameter, a body of about 110mm length and 40mm internal diameter, a slot of about 2mm width, a piston weight of about 3gm, a spring with a rate of about 40gm/cm, and an indicator movable in response to an acceleration greater than 3g, which prototype provided results comparable with existing instruments over a range from 20 to 800 liters/minute expiration rate. However, the characteristics of the instrument can be modified readily by changing the spring 60, which is easily accessible, and changing the scale.

A further advantage in manufacture can arise from the fact that the piston 50 need not be a precise fit on the rod 40 and within the cylinder 10, but can be free to wobble slightly by virtue of the relatively short bore portion 55. This eases manufacturing tolerances and assembly, and any resultant leakage of expired air past the piston during use of the instrument is equivalent simply to a prolongation of the slot 15 in the reducing direction of the scale 16. Indeed, no significant error is found to arise in use of the feature. However, available moulding techniques should allow the provision of sufficiently accurate tolerances that little leakage past the piston occurs, and the piston can accordingly have a uniform bore in place of 54,55 if preferred.

While the invention has been more particularly described with reference to the embodiment of FIGS. 1–8, it is not intended to be limited thereby, but is capable of modification and variation within the scope of the appendant claims. Indeed the invention is currently being further developed for the purposes of large scale production. In this development one end member is integrally moulded with the cylinder, and both of the end members are apertured to form a more pronounced spoked wheel form to enhance air flow therethrough while still affording a rigid construction. Also, entry of the spring-loaded indicator member during assembly is facilitated by opening the associated slot at one end of the cylinder, this opening being closed by a key equivalent to 26 in FIG. 2 on the separable end member. In this connection, a simplified integral sprung indicator member is now preferred, such member having a general form as illustrated by FIGS. 9 and 10. The member is formed from a metal blank denoted at 90 in FIG. 9 which blank has end portions 91 and 92 of greater width than the associated slot, such portions being connected by a strip 93 narrower than the relevant slot. This blank 90 is formed to a generally spiral shape as shown in FIG. 10 to serve as a spring. In use, the strip 93 is engaged in the cylinder slot 15 denoted in broken outline with one end portion 91 located within the cylinder to engage the piston disc 51 also denoted in broken outline, and the other end portion 92 located in the groove 12 outside the cylinder. It is to be noted that the spiral shape is orientated relative to the piston so that movement of the latter in the direction denoted by arrow due to expiration by a user will urge the piston against portion 91 to open the spiral shape and so facilitate movement of the member, and the same action occurs when subsequently pushing the portion 92 in the opposite direction to reset the member. The portion 91 will, of course, need to be formed to a laterally curved shape for accommodation in the cylinder, and the portion 92 is conveniently formed to incorporate a marker and to have an unflattened shape to facilitate pushing, such formations being denoted by broken fold lines.

I claim:

1. A ventilatory capacity measuring instrument for measuring the maximum flow rate of a single forced expiration, comprising:

a hollow cylindrical body;

first and second apertured end members connected in respective ends of said body, with at least one of said members being separable from said body; a hollowed mouthpiece connected with said first end member to extend outwardly therefrom relative to said body, and communicated with the hollow of said body by way of the aperturing of said first end member; a rod respectively connected at its ends with said end members extending coaxially within said body;

an annular piston slidably mounted on said rod and wholly confined within said body;

a constant rate spring operably connected between said piston and body, in the annular space between said body and rod, to apply a linearly increasing bias against movement of said piston from said first end member towards said second end member;

a slot of uniform width formed in and extending along said body in a longitudinal direction; an indicator mounted in said slot between said piston and said second end member, and separably engaged with said piston for movement therewith towards said second end member but separate movement towards said first end member, said indicator including spring retaining means for engaging the parts of said body bordering said slot; and a non-linear scale extending along said body alongside said slot.

2. An instrument as in claim 1 wherein said indicator is of integral elongated construction comprising a first widened end portion seated on the exterior surface of said body to laterally bridge said slot, a narrowed central portion connected at one end to said first portion and extending through said slot into said body, and a second widened end portion connected with the other end of said central portion and seated on the interior surface of said body to bridge said slot, said construction extending in a spiral configuration in a longitudinal axial planar direction of said body with said spiral configuration opening towards said piston.

3. An instrument as in claim 2 wherein said body is formed with a longitudinally-extending groove in its exterior surface, said slot is sited in said groove, and said indicator is seated in said groove.

* * * * *